(12) United States Patent
Cantini et al.

(10) Patent No.: US 10,336,350 B2
(45) Date of Patent: Jul. 2, 2019

(54) AXLE OF WHEEL SETS AND RESPECTIVE METHOD FOR THE ULTRASOUND INSPECTION

(71) Applicant: LUCCHINI RS S.P.A., Lovere (BG) (IT)

(72) Inventors: Stefano Cantini, Lovere (IT); Steven Cervello, Lovere (IT)

(73) Assignee: LUCCHINI RS S.P.A., Lovere (BG) (IT)

(*) Notice: Subject to any disclaimer, the term of this patent is extended or adjusted under 35 U.S.C. 154(b) by 80 days.

(21) Appl. No.: 15/129,129

(22) PCT Filed: Mar. 17, 2015

(86) PCT No.: PCT/IB2015/051934
§ 371 (c)(1),
(2) Date: Sep. 26, 2016

(87) PCT Pub. No.: WO2015/145303
PCT Pub. Date: Oct. 1, 2015

(65) Prior Publication Data
US 2017/0106881 A1 Apr. 20, 2017

(30) Foreign Application Priority Data
Mar. 27, 2014 (IT) .............................. BS2014A0074

(51) Int. Cl.
*G01N 29/24* (2006.01)
*G01N 29/04* (2006.01)
(Continued)

(52) U.S. Cl.
CPC .............. *B61F 15/20* (2013.01); *B60B 17/00* (2013.01); *B60B 35/025* (2013.01); *B60B 35/04* (2013.01);
(Continued)

(58) Field of Classification Search
CPC ...... G01N 29/04; G01N 29/24; G01N 29/221; G01N 29/225; G01N 29/2487;
(Continued)

(56) References Cited

U.S. PATENT DOCUMENTS 3,685,350 A * 8/1972 Pettinato ................ G01N 29/24
310/336
5,131,276 A * 7/1992 Kibblewhite ......... B06B 1/0662
29/595
(Continued)

FOREIGN PATENT DOCUMENTS

DE 10 2004 012667 A1 10/2005
WO 2009067773 A1 6/2009

OTHER PUBLICATIONS

Rene Sicard et al: "Phased Array Scanner Head for Train Axle Inspection" 18th World Conference on Nondestructive Testing, Apr. 16-20, 2012, Durban, South Africa, pp. 1-10.

*Primary Examiner* — Natalie Huls
*Assistant Examiner* — Suman K Nath
(74) *Attorney, Agent, or Firm* — Volpe and Koenig, P.C.

(57) ABSTRACT

An axle of railway wheel sets and a corresponding method for the ultrasound inspection are described. A blind hole, coaxial to the axle and sized to accommodate an ultrasonic probe, is obtained in each end of the axle. Main holes are intended to accommodate the probe holder containing a plurality of ultrasonic transducers for the inspection of the axle from the inside of the hole. The main advantage is to facilitate the propagation of the ultrasounds without being subjected to the interference caused by the geometric discontinuities normally present at the ends of the axles thereby minimizing false positives in the readings of the echoes.

9 Claims, 3 Drawing Sheets

(51) Int. Cl.
*G01M 17/10* (2006.01)
*B61F 15/20* (2006.01)
*B60B 17/00* (2006.01)
*B60B 35/02* (2006.01)
*B60B 35/04* (2006.01)

(52) U.S. Cl.
CPC ............ *G01M 17/10* (2013.01); *G01N 29/04* (2013.01); *G01N 29/24* (2013.01); *B60B 2900/3316* (2013.01); *B60B 2900/541* (2013.01); *B60Y 2200/30* (2013.01); *G01N 2291/044* (2013.01)

(58) Field of Classification Search
CPC ...... G01N 29/26; G01N 29/265; G01N 29/28; G01N 2291/044; G01N 2291/2693; G01N 2291/2696; G01N 2291/105; B60B 2900/541; B60B 35/12; B60B 29/3316; B60Y 2200/30; B61F 99/00

USPC .... 73/627, 620, 622, 623, 625, 641, 115.07, 73/115.08

See application file for complete search history.

(56) References Cited

U.S. PATENT DOCUMENTS

| | | | | |
|---|---|---|---|---|
| 5,426,978 | A * | 6/1995 | Imai | G01B 17/00 367/99 |
| 5,708,208 | A * | 1/1998 | Bonitz | G01N 29/223 73/598 |
| 8,966,984 | B2 * | 3/2015 | Lesage | G01N 29/0609 73/602 |
| 2001/0052258 | A1 * | 12/2001 | Ehrlich | B60T 8/00 73/115.08 |
| 2005/0022602 | A1 * | 2/2005 | Falsetti | G01N 29/11 73/627 |
| 2007/0006658 | A1 * | 1/2007 | Kennedy | G01N 29/265 73/622 |
| 2014/0000371 | A1 * | 1/2014 | Engl | G01N 29/2437 73/640 |

* cited by examiner

AXLE OF WHEEL SETS AND RESPECTIVE METHOD FOR THE ULTRASOUND INSPECTION

SCOPE OF THE INVENTION

The present invention is in the field of railway vehicles and, in particular, relates to an axle of wheel sets designed so as to facilitate its ultrasound inspection.

STATE OF THE ART

In railway engineering, the expression "wheel set" is meant to identify the group of elements comprising two wheels and the corresponding connecting axis, or axle.

The railway wheel sets support the railway vehicle on the rails. Therefore, continuous mechanical and thermal stresses are imposed by the trains to wheels and axles of the respective wheel sets.

Vehicle loads, driving conditions and small discontinuities of the railway line, which can cause wagon jerks, as well as collisions against the ballast or another material, etc., cause mechanical stresses. The continuous change of external temperature and humidity the trains face on their way and between day and night, cause the thermal stresses.

The mechanical and thermal stresses can cause cracks to propagate in the axle. To pre'vent a crack from being generated and propagated in an axle till its structural failure, which can lead to serious accidents, in many countries periodical checks of the axle integrity are required by law.

A non-invasive test is carried out by inspecting the wheel set by means of ultrasounds generated by a specific device, commonly known as 'rotating probe', comprising a plurality of longitudinal-waves ultrasonic transducers and the respective housing called probe-holder. Usually, ultrasounds are generated by piezoelectric and/or electrostrictive and/or magnetostrictive crystals.

The transducers are arranged in the housing around a longitudinal axis and are converging or diverging, that is to say the ultrasound beam, in form of longitudinal waves, emitted by each transducer will propagate in the steel of the axle forming a corresponding angle with the longitudinal axis.

The device is temporarily constrained to one end, or 'head', of the axle by means of magnets, the axle being in its respective use conditions, that is painted, with all components assembled (wheels, brake disks, reduction gears) and integral with the bogie mounted below the railway coach. In particular, the device is constrained to an axle head so that the rotation axis of the axle collimates with the longitudinal axis of the device itself. In this arrangement, ultrasound beams emitted by the transducers propagate through the axle steel; if the transducers are converging, then they generate an ultrasound beam having an axis intersecting the rotation axis of the axle and, conversely, if the transducers are diverging then they generate an ultrasound beam having the axis not intersecting the rotation axis of the axle.

A propagation angle of the ultrasound beam is associated with each transducer: for example if the rotating probe comprises three transducers, then the respective three ultrasound beams propagates in the axle according to three different corresponding angles.

An ultrasonic coupling agent, for example oil, is interposed among the transducers and the outer surface of the axle end in order to maximize the transmission of the ultrasound beam.

A technician activates one transducer at a time and rotates the probe (namely, rotates the housing and the transducers therein), so that the transducer each time activated carries out a complete turn thereby covering a corresponding annular portion of the axle with its ultrasound beam. The shape of the portion intercepted by each ultrasound beam depends on the width of the beam itself and the penetration depth of the beam into the steel of the axle.

Echoes generated by the axle in response to the propagation of the ultrasonic beam in each transducer, at multiple angular positions of the probe, are collected and analyzed.

The reason is as follows: trespassing of the ultrasonic beam is contrasted through two materials having a different acoustic permeability (in the specific case the steel of the railway axle and the air present in discontinuities appearing on the surface). In particular, if there is a discontinuity, for example at axle flaws such as cracks, notches or fractures, the ultrasonic waves are reflected, refracted and diffused.

Therefore, by analyzing the echoes generated by the ultrasonic beam of a transducer, it is possible to detect flaws in the axle in the portion intercepted by that transducer. The repetition of the analysis for all the transducers and for both ends of the axle makes it possible to inspect the axle along almost its entire length.

In practice, the rotating probe is combined with a reading device allowing the detection of the echoes and the visualization of the corresponding graphs. In the graphs, flaws of the axle correspond to peaks. The analysis of the echoes allows the identification of the position and size of the flaws so as to distinguish the potentially dangerous ones.

The above described procedure also comprises the application of ultrasonic probes called "phased array" formed by a set of aligned probes which can provide, if properly supplied, an instantaneous two-dimensional analysis.

For example, the article "*Phased Array Scanner Head for Train Axle Inspection*", by René SICARD, Gérard LANDRY, Hussam SERHAN, presented at the '18th World Conference on Nondestructive Testing, 16-20 Apr. 2012, Durban, South Africa' describes and shows images of an ultrasound verification technique by a rotating probe of the "phased array" type.

A drawback found during inspections is associated with the geometry of the axles of the wheel sets.

At the axle ends threaded blind holes are obtained, which are parallel to the rotation axis of the axle and intended to receive fastening pins of the wheel bearings. The holes behave as discontinuities, thus adversely affecting the inspection with the rotating probe.

In fact, the threaded holes in the axle heads are directly in line with the paths followed by the transducers of the rotated probe. Unavoidably, the propagation of the ultrasonic beams into the steel of the axle is adversely affected.

Therefore, the technician performing the axle inspection has to adjust the radial position of the transducers with respect to the longitudinal axis and the respective convergence/divergence angles, in order to prevent ultrasonic beams from intercepting the threaded holes thus undergoing reflections, refractions and diffusions and causing the reading of false positives (not relevant readings). This is time-consuming and requires some experience by the technician responsible for the inspection.

SUMMARY OF THE INVENTION

It is therefore an object of the present invention to provide an axle designed so as to facilitate as much as possible the inspection by means of ultrasonic probes and maximize the inspection quality.

It is also an object of the present invention to provide a method for the inspection of the axles of railway wheel sets with ultrasonic probes, in which false positives are absent or present in minimum number.

Therefore, a first aspect of the present invention concerns an axle of railway wheel set according to claim 1.

In particular, the axle extends along a longitudinal axis between two ends, each intended to support at least one railway wheel and the respective bearing so as to form a wheel set.

Unlike traditional solutions, in each end is obtained a blind hole, named main hole, coaxial to the axle and sized to accommodate an ultrasonic probe, thereby aiding the effective inspection of the axle itself.

Main holes should not be mistaken for the countersinks which sometimes are on the ends of the axles for centering the axle during some operations, such as turning, and/or for allowing traditional probes to be aligned with the axis of the axle. When these countersinks are used also for ultrasonic checks, they are intended to receive only an aligning pin of the traditional probes, the transducers always remaining outside the axle. The function and the configuration of the main holes are completely different, as they are intended to accommodate at least the entire portion of the probes provided with the transducers, for the inspection from the inside of the hole.

The main advantage provided by the proposed solution is to allow the probe to be inserted in the axle end for a certain length, so that ultrasounds are able to propagate without the interference given by the geometric discontinuities normally present at the axle ends. In other words, the solution proposed provides a drastic reduction in false positives.

Preferably, the main holes are accessible from the outside so as to allow the technician to insert the probe and, more preferably, are circular to allow the rotation of the ultrasonic sound inside them. It should be noted that the above described small countersinks do not allow the insertion of an ultrasonic probe.

Practically, in the axle ends additional longitudinal holes named secondary holes, are obtained and engage the fastening screws of the bearing of the respective wheel. In the axles there are often three secondary holes. In this circumstance, the secondary holes are obtained around the respective main hole, i.e. they are not coaxial to the axle but they have an axis parallel to the axis of the axle. The secondary holes have a diameter which is considerably smaller than the diameter of the main holes.

In the preferred embodiment, the main holes extend into the axle more deeply than the secondary holes. Thanks to this feature, the ultrasounds generated by the probe are not affected by the presence of the secondary holes, which are actually bypassed by the ultrasounds so that they do not generate false positives in the echoes.

At least one portion of the outer surface of each end, named journal, is rectified to allow the bearing of a wheel to be fitted. Preferably, the main holes extend deeply into the axle for a length between 50% and 120% of the longitudinal extent of the journal. In this way, the ultrasounds generated by the probe are not affected by the presence of the bearings or they are affected only partially.

Therefore, a second aspect of the present invention concerns a method for the inspection of axles of railway wheel sets according to claim 7.

In particular, the method comprises the steps of:

a) providing a wheel set according to the present invention, as above described, and an ultrasonic probe provided with one or more transducers;

b) inserting the ultrasonic probe alternately in the main holes of the two ends of the axle;

c) activating one transducer at a time and rotating the probe in the main hole, so that the probe performs one or more complete turns;

d) detecting the echoes propagating in the axle and analysing them to identify possible defects or discontinuities.

The techniques for the echo analysis are known and will be not detailed herein.

It should rather be noted that the described method allows the effective inspection of the axles thereby avoiding false positives normally caused by the fastening holes of bushings or bearings.

Preferably, the application of a coupling agent, e.g. oil, between the ultrasonic probe and the bottom of the main holes is also provided.

Preferably, the probe is rotated at a speed lower than, or equal to, 30° per second so that the transducer selected in turn covers a corresponding penetration cone in the axle.

Preferably, the probe is provided with one or more outer sealing gaskets, for example O-rings. The gaskets have the function to adhere to the side wall of the main bore, so that a coupling agent is sealed. A coupling chamber, basically a volume, is delimited by the bottom and the side wall of the main hole, by the ultrasonic probe and the respective gaskets. The coupling agent is circulated in the coupling chamber and the gaskets prevent it from spilling.

A third aspect of the present invention concerns a rotating probe according to claim 10 for the ultrasound inspection of the above described axles.

The ultrasonic probe comprises a body arranged to accommodate one or more ultrasonic transducers, which can be converging or diverging (in the sense given above to these terms) or have an adjustable angle. One or more outer sealing gaskets are arranged on the body in such a way that the probe body can be inserted into the main holes of the axle so that the coupling agent is sealed. According to this arrangement, the probe body behaves as a piston inserted in one of the main holes of the axle, with the gaskets sliding on the inner wall of the hole.

Preferably, the transducers are arranged at a front face of the probe body, the face being intended to be pointed towards the bottom of a main hole of the axle. The probe comprises adduction means of a coupling agent to the front face. For example, these adduction means comprise a recirculation pump, also external, a feeding duct preferably opening at the front face and a drain for the discharge of the coupling agent from the front face, so that the coupling agent could be circulated among the transducers and the axle, in the so-called coupling chamber, when the probe is inserted in a main hole.

BRIEF DESCRIPTION OF THE DRAWINGS

Further characteristics and advantages of the invention will be more evident from a review of the following specification of a preferred, but not exclusive, embodiment, shown for illustration purposes only and not limiting, with the aid of the attached drawings, in which.

DETAILED DESCRIPTION OF THE INVENTION

Figure 1:
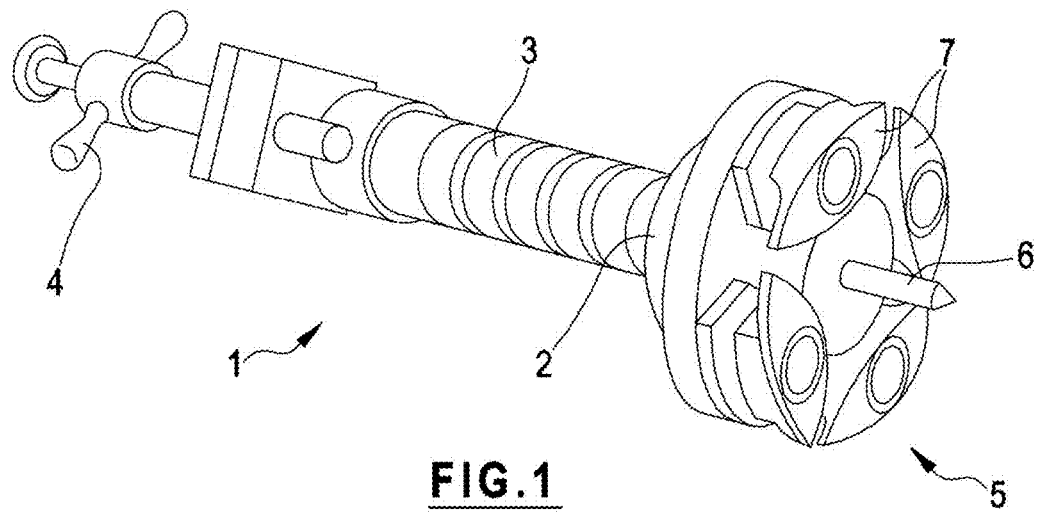
FIG. 1 is a perspective view of a rotating ultrasonic probe of traditional type.

FIG. 1 shows a rotating ultrasonic probe 1 of traditional type, provided with a body 2 in its turn equipped with a gripping handle 3 and a turning knob 4, the latter being manually operable by the technician in order to rotate the probe 1 during an axle inspection. Ultrasonic transducers 7 are mounted in the head portion of the probe at the front face 5. In the illustrated example four transducers 7 are shown, although they can generally be in different number.

The aligning pin 6 protrudes from the front face 5 of the probe to be inserted in a corresponding countersink formed in the front of the ends of the traditional axles. The pin 6 allows the technician to easily align the probe 1 on the longitudinal axis of the axle to be inspected.

As explained above, the transducers 7 can be converging or diverging or they are mounted on the body 2 of the probe 1 so that the technician can adjust their angle according to the needs.

Figure 2:
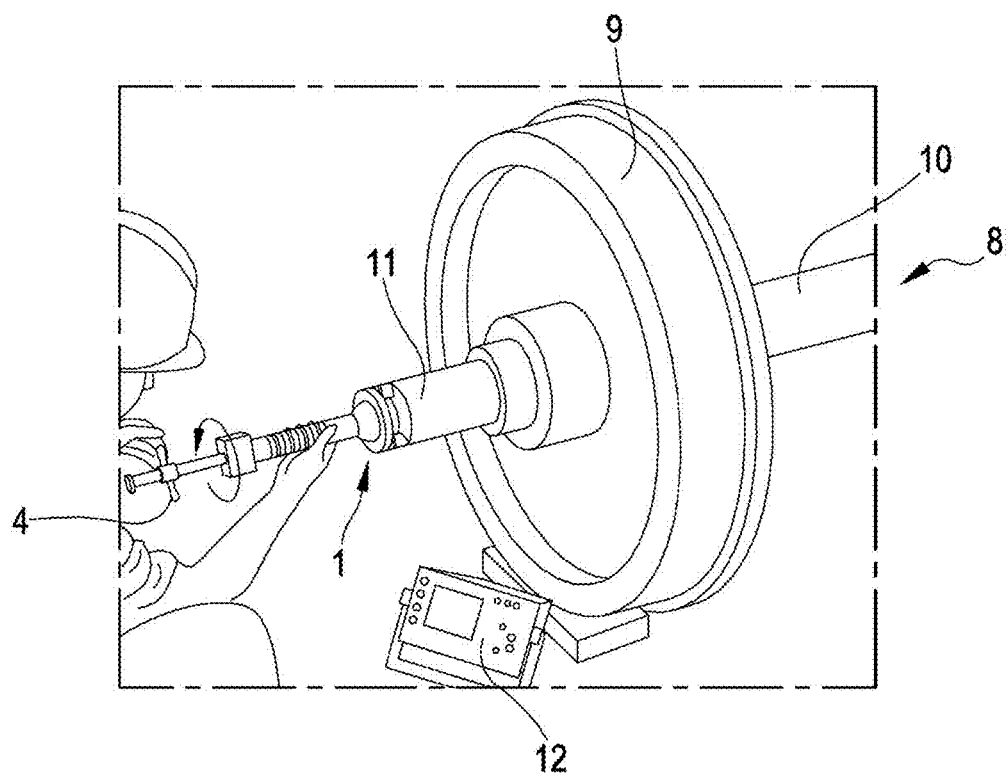
FIG. 2 is a perspective view of a wheel set traditionally inspected by the probe shown in FIG. 1.

FIG. 2 shows a portion of a traditional railway wheel set 8 comprising wheels 9 and an axle 10. A technician moved the probe 1 in abutment against the end 11 of the axle 10 so that it is operatively coupled to the axle 10. In order to rotate the probe 1 by at least 360°, thereby rotating the ultrasound beam generated by the activated transducer 7, the technician turns the knob 4.

By means of the detecting and analyzing device 12, the technician analyses the echoes generated in the axle 10 by the ultrasounds propagating in the material of the axle itself. Peaks correspond to the detected discontinuities. Also by taking advantage of its experience, the technician has to distinguish the false positives from possible real flaws of the axle 10.

Figure 3:
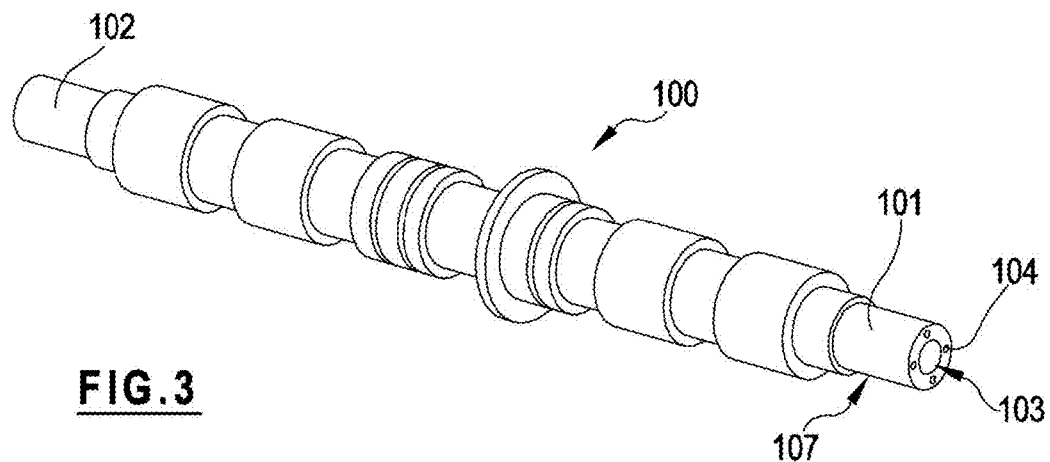
FIG. 3 is a perspective view of an axle of railway wheel sets according to the present invention.

FIG. 3 shows an axle 100 according to the present invention which is different from the prior art because it has two blind holes 103 each formed in one end 101, 102. The outer surface of the ends 101, 102 is at least partially rectified in order to allow the bearings 105 of the wheels to be fitted. The rectified surface 107 is named journal.

Figure 4:
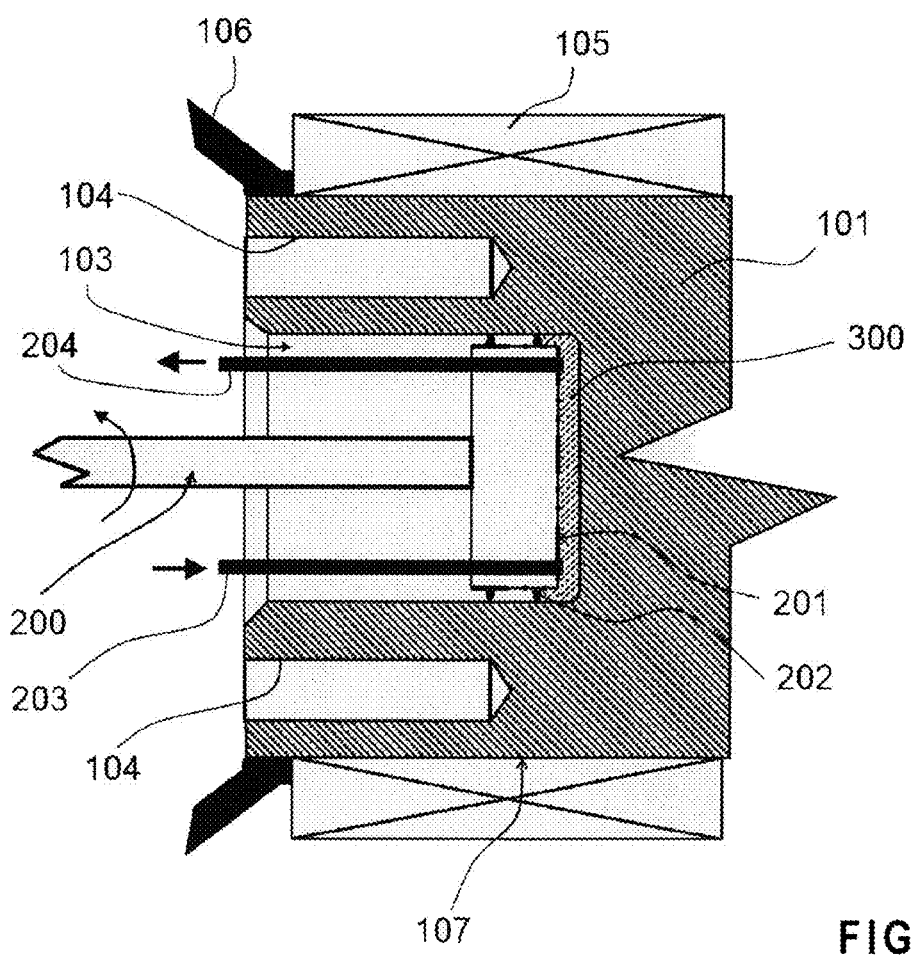
FIG. 4 is a perspective view of an axle and a probe according to the present invention, in use.

FIG. 4 explains the advantage given by the blind holes 103, hereinafter named main holes.

In each end 101, 102, the main holes 103 are coaxial to the axle 100 and are radially internal with respect to the secondary holes 104 for fastening the bushing of the bearing 105 of the wheel (not shown).

An ultrasonic probe 200 according to the present invention can be inserted into the main holes 103 for the axle inspection. As shown in FIG. 4, the probe 200 is not simply in abutment against the end 101, 102, as in the prior art, but is inserted into the axle 100 up to the bottom of the main hole 103 and is rotated therein by the technician.

This solution offers the advantage that the ultrasound generated by the probe 200 does not intercept nor the secondary holes 104 or the bearing 105 (at most the latter, but only partially).

The Applicant carried out tests which showed that, compared to a traditional axle, the proposed solution involves a much smaller number of false positives, which means less peaks in the readings of the echoes.

Preferably, as shown in figure, when the technician inserts the probe, a coupling chamber 300 is formed between the probe 200 and the bottom and the side wall of the main hole 103. In particular, the coupling chamber 300 is delimited by the bottom and the side wall of the hole 103, by the front face 201 of the probe 200 (on which the transducers not shown for the sake of simplicity are provided) and by at least one sealing gasket 202, e.g. an O-ring, which encircles the probe 200 setting it up as a piston with respect to the hole 103.

A coupling agent is circulated inside the coupling chamber 300, as shown by the arrows, by means of feeding ducts 203 and drains 204, connected to an outer recirculation pump (not shown).

The reference 106 indicates a wheel cover that prevents the coupling agents from spilling onto the probe 200.

The bearing 105 is fitted to the journal 107. Preferably, the main hole 103 has a depth at least equal to 50% of the longitudinal extent of the journal 107.

Figure 5:
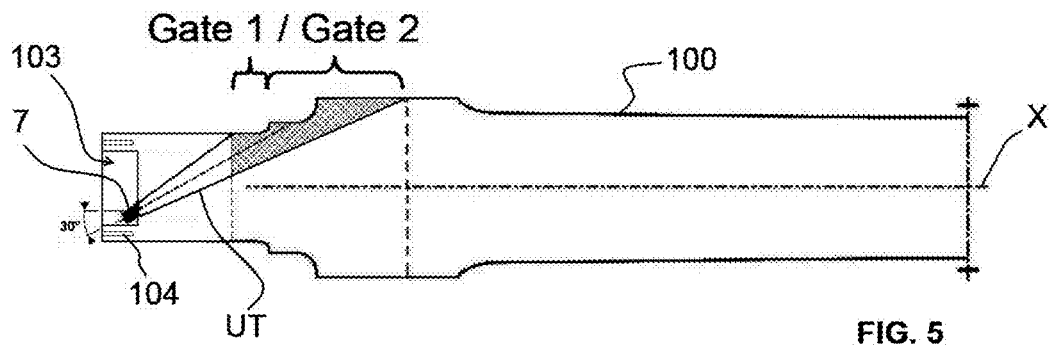
FIG. 5 is a schematic sectional view of an axle according to the present invention, during the inspection.

Referring to FIG. 5 showing a partial section of the axle 100 during an inspection, the technician activates one transducer 7 at a time, among those mounted on the probe 200 (not shown in this figure for the sake of simplicity). Each transducer is mounted so as to form a corresponding angle with the longitudinal axis X of the axle 100. In the example shown in figure, the transducer 7 forms a 30° angle with respect to the longitudinal axis X.

The transducer 7 generates an ultrasound beam UT that propagates into the axle 100, starting from the bottom of the main bore 103. By rotating the probe 200, the ultrasonic beam UT is also displaced in order to inspect a corresponding annular portion of the axle 100. The areas indicated as 'Gate 1' and 'Gate 2' correspond to two separate areas on the graph shown in FIG. 7.

Figure 6:
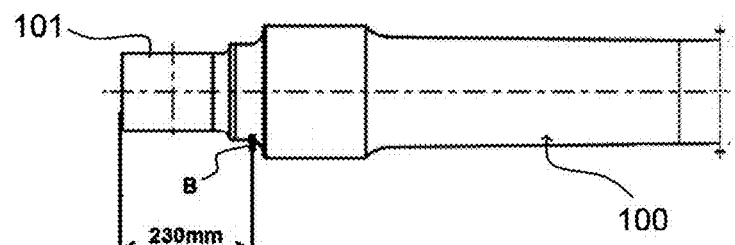
FIG. 6 is a side schematic view of the axle shown in FIG. 5.

FIG. 6 shows the same axle 100 of FIG. 5, in a side view rather than in cross section. A notch B, schematically shown as a black rectangle, was made in the axle at a distance of 230 mm from the edge of the end 101.

Figure 7:
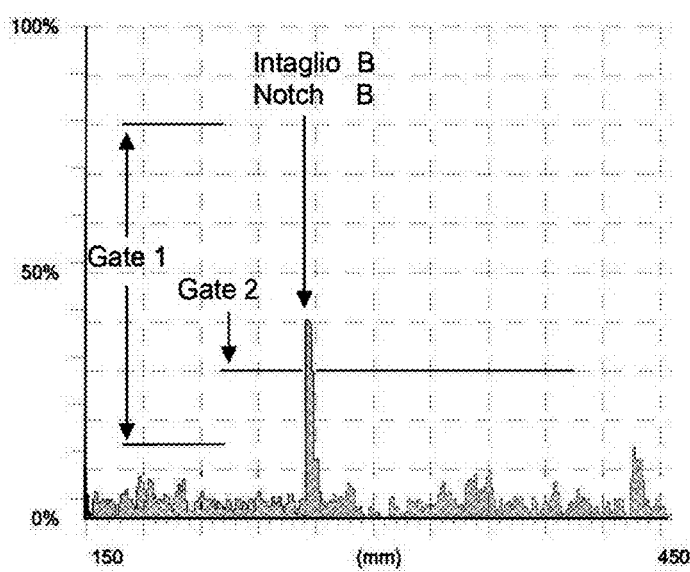
FIG. 7 is a diagram of the echoes detected during an inspection of the axle shown in FIG. 5.

FIG. 7 shows the diagram corresponding to the readings of the echoes of the ultrasound beam UT. The distance is indicated on the x coordinate and the percentage of reflected ultrasonic energy with respect to a standard quantity on the y coordinate. At the notch B there is a peak showing to the technician that the notch is just 130 mm from zero. The secondary holes 104 and the journal bearing of the axle 100 do not affect the reading.

The invention claimed is:

1. An axle (100) of railway wheel set extending along a longitudinal axis (X) between two ends (101, 102), the ends (101, 102) each having a journal (107), configured to support a railway wheel and a respective bearing (105) so as to form a wheel set, wherein each end (101, 102) comprises a blind main hole (103), coaxial with the axle (100) and dimensioned to accommodate an ultrasonic probe (200), wherein each blind main hole (103) has a depth within a longitudinal extent of the journal (107) and is dimensioned to receive the ultrasonic probe (200) for inspection of the axle (100) ahead of the probe.

2. The axle (100) according to claim 1, wherein the main holes (103) are accessible from the outside and are circular to allow rotation of the ultrasonic probe (200) inserted therein.

3. The axle (100) according to claim 1 further comprising, in both ends (101, 102), additional longitudinal secondary holes (104), which engage fastening screws of the bearing (105) of the respective wheel, or its bushing, and wherein the secondary holes (104) are arranged around the respective main hole (103), not coaxial with the axle.

4. The axle (100) according to claim 3, wherein the secondary holes (104) have a diameter that is considerably smaller than the diameter of the main holes (103).

5. The axle (100) according to claim 3, wherein the main holes (103) extend longitudinally into the axle (100) for a length that is longer than a length of the secondary holes (104), so that ultrasounds made by the probe (200) are not affected by the presence of the secondary holes (104).

6. The axle (100) according to claim 1, wherein at least one journal (107) of an outer surface of both ends, is configured to allow the bearing (105) of a wheel to be fitted, and wherein the main holes (103) extend into the axle (100) for a length between 50% and 120% of a longitudinal extent of the journal (107), so that ultrasounds generated by the probe (100) are not affected by the presence of the bearings (105) or are affected only partially.

7. A method for the ultrasound inspection of a railway wheel set, the method comprising the steps of:
   a) providing a wheel set provided with an axle (100) according to claim 1 and an ultrasonic probe (200) provided with one or more transducers (7);
   b) inserting the ultrasonic probe (200) alternately in the main holes (103), within a longitudinal extent of the journal (107), of the two ends (101, 102) of the axle;
   c) activating one transducer (7) at a time and rotating the probe in the main hole, within a longitudinal extent of the journal (107), so that the probe performs one or more complete turns;
   d) detecting echoes propagating in the axle (100) and analyzing the echoes to identify possible defects or discontinuities (B).

8. The method according to claim 7, further comprising one or more of the following additional steps:
   e) applying a coupling agent between the ultrasonic probe (200) and the bottom of the main holes (103);
   f) rotating the probe at a speed lower than, or equal to, 30° per second.

9. The method according to the claim 8, wherein step e) provides for:
   applying one or more outer sealing gaskets (202) to the ultrasonic probe (200), and
   defining a coupling chamber (300) limited by a bottom of the main hole (103), by a side wall of the main hole (103), by the ultrasonic probe (200) and the respective gaskets (202), and wherein the coupling agent is circulated in the coupling chamber (300).

* * * * *